United States Patent [19]

Moore, Jr.

[11] Patent Number: 4,547,189

[45] Date of Patent: Oct. 15, 1985

[54] INSULIN SYRINGE INJECTOR APPARATUS WITH AUTO-ASPIRATOR FEATURE

[75] Inventor: Paul C. Moore, Jr., Matoaca, Va.

[73] Assignee: John A. Long, Petersburg, Va. ; a part interest

[21] Appl. No.: 587,171

[22] Filed: Mar. 5, 1984

[51] Int. Cl.[4] ............................................. A61M 5/20
[52] U.S. Cl. ................................................... 604/136
[58] Field of Search ................. 604/186, 134, 135, 136

[56] References Cited

U.S. PATENT DOCUMENTS

| | | | |
|---|---|---|---|
| 2,150,738 | 3/1939 | Dunajeff | 604/135 |
| 2,671,448 | 3/1954 | Harnisch | 604/136 |
| 3,880,163 | 4/1975 | Ritterskamp | 604/136 |
| 3,941,130 | 3/1976 | Tibbs | 604/136 |
| 4,333,459 | 6/1982 | Becker | 604/135 |

*Primary Examiner*—John D. Yasko
*Attorney, Agent, or Firm*—Mason, Fenwick & Lawrence

[57] ABSTRACT

An auto-aspirating hypodermic syringe supporting and operating device for self-administered injection of hypodermic medication, insulin or the like comprising an elongated thin main plate member having longitudinal slots, a carriage assembly slidably mounted on the plate member for reciprocative longitudinal movement through projecting and retracting strokes including a spring biased syringe carrier member having front and rear holder portions to removably hold the barrel and a back member fixed to the carrier member to slide longitudinally with the carrier member. A pivoted latch trigger member is pivoted on the plate member to latch the carriage assembly in a cocked position and a stop supporting bracket extends from the plate member having movable stop members and a stop positioning cam plate to position the said stop members at an intercepting first position and retracted second position relative to an enlarged head of the plunger.

20 Claims, 9 Drawing Figures

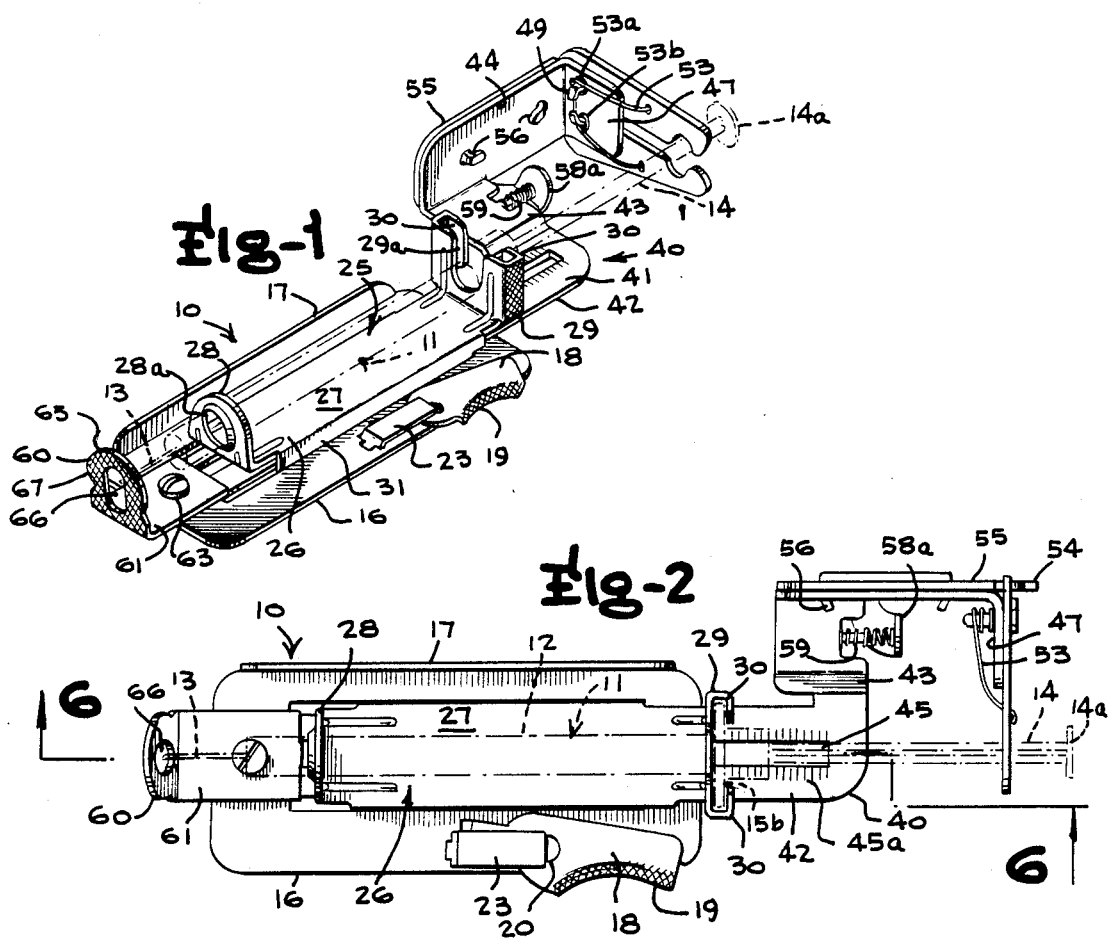
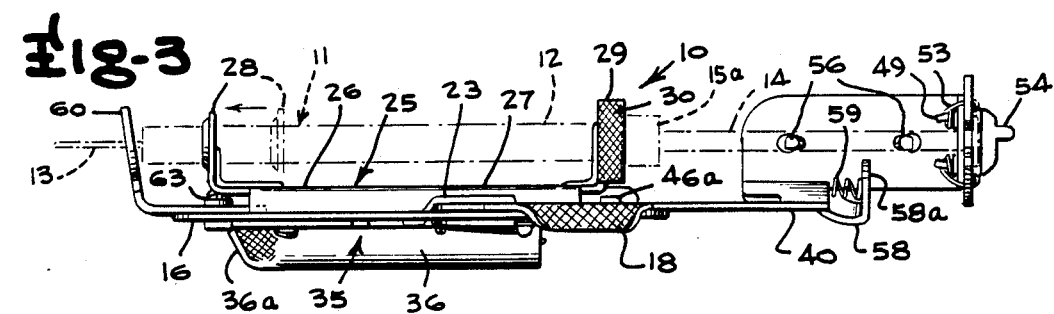
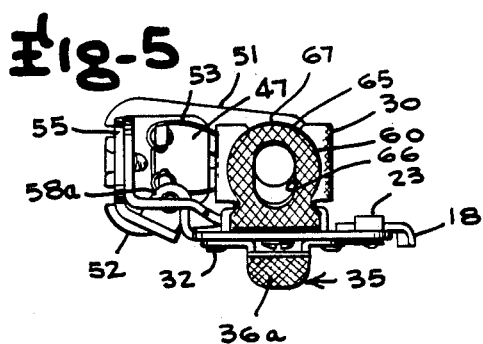
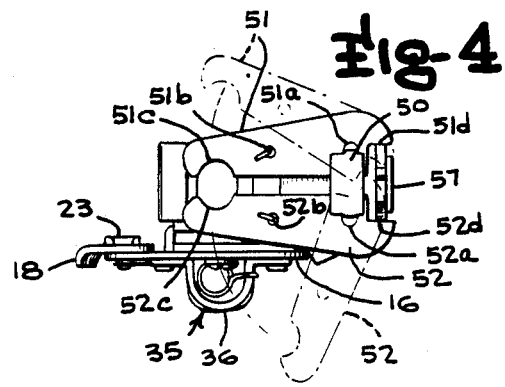

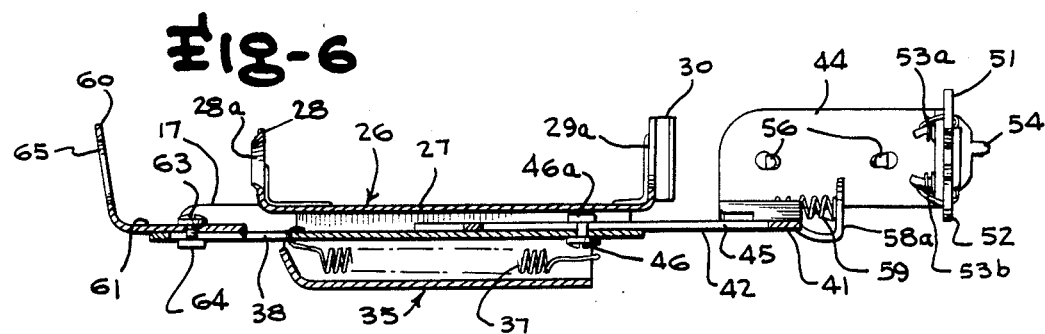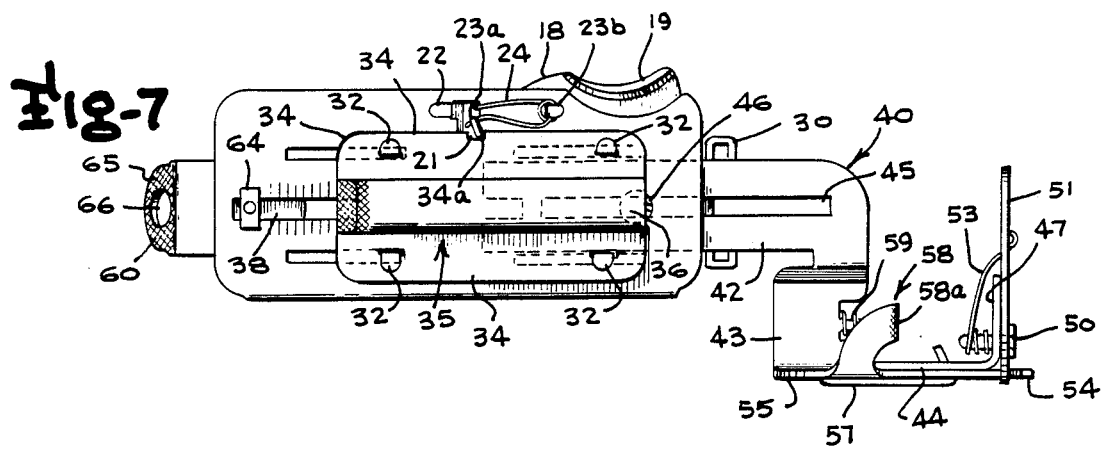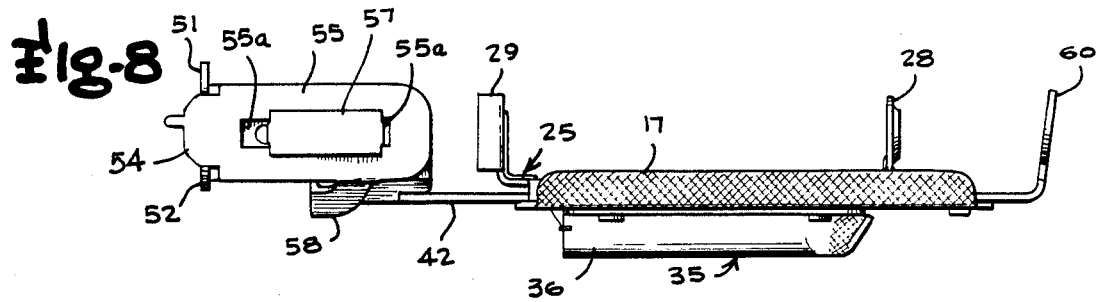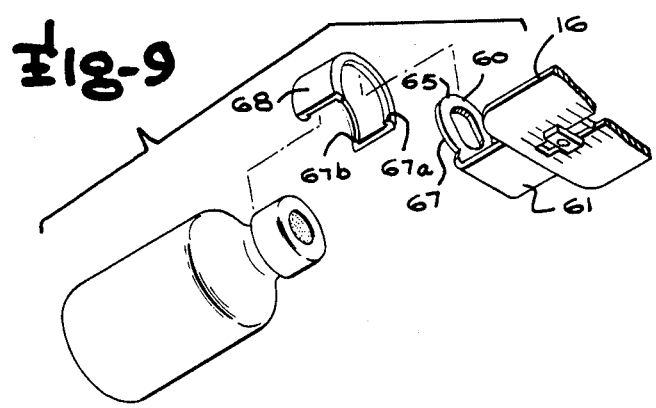

INSULIN SYRINGE INJECTOR APPARATUS WITH AUTO-ASPIRATOR FEATURE

BACKGROUND AND OBJECTS OF THE INVENTION

The present invention relates in general to hypodermic syringe supporting and operating mechanisms particularly for hypodermic injections of insulin or other fluid doses by the patient himself, and more particularly to a supporting and operating device for hypodermic syringes for removably supporting the syringe, measuring the dose loaded into the syringe, activating the syringe to project the needle into the body tissue to be injected, and automatically aspirating the syringe to withdraw a noticable quantity of blood if a vein has been penetrated.

Heretofore, many spring actuated support devices for hypodermic syringes have been provided to support the plunger and barrel of the syringe and propel them and the needle to the desired injection site in body tissue. Many of these have a foot or contact formation designed to be placed against the external surface of the patient's body into which the needle is to be injected, and a trigger or other release mechanism which permits a cocked spring to propel the needle into the injection site, following which the plunger is mechanically operated to discharge the dose through the needle into the body tissue at the tip of the needle. Usually these are made with expensive parts or of relatively complex construction, increasing difficulty of operation, cost of manufacturing, and possibility of frequent mechanical breakdown. Also, such prior art syringe supporting and injecting devices simply propel the needle and plunger through an advanced stroke when the cocked spring associated therewith is released, having no operating features which provide any indication of whether or not a vein may have been penetrated during injection of the needle into the body. Particularly in the case of insulin injection, it is essential that the tip of the needle not terminate in a vein at the end of the advance stroke, since insulin must never be injected directly into a vein.

Applicant is aware of one prior U.S. Pat. No. 3,702,608, to Tibbs, disclosing a hypodermic syringe supporting and operating device, which also includes operating features whereby aspiration of the syringe occurs during the projection stroke by means of a complex mechanism wherein a syringe plunge holder is supported for reciprocal shifting during the latter part of the injector stroke to achieve aspiration. However, such a construction is complex and expensive to manufacture and a simplification of the supporting device for ease of use and simplicity and economy of manufacture is desired to provide a syringe support and injector device which will have an autoaspirator feature to withdraw a visibly notable amount of blood into the syringe at the completion of the penetration stroke if the end of the needle is located in a vein.

An object of the present invention is the provision of a simplified and less expensive mechanical supporting and operating device for removably receiving and supporting a conventional hypodermic syringe, to support the syringe for spring-driven projection over a predetermined distance to insert the needle to a determined depth into body tissue disposing the tip of the needle a desired distance from a contact foot formation adapted to be placed in abutment with the skin of the patient or user, and wherein the plunger of the syringe is retracted a short distance automatically during the final portion of the projection stroke to aspirate the syringe so that blood will be aspirated into the syringe and be visible if the needle is located in a vein.

Another object of the present invention is the provision of a hypodermic syringe support and operating device as described in the preceding paragraph, wherein a driving spring and releasable latch and trigger mechanism is provided in an inexpensive, simple and reliable mechanical structure.

Another object of the present invention is the provision of a hypodermic syringe support and operating mechanism as described in the two immediately preceding paragraphs, wherein easily movable caliper-type stop arms and spring structure is provided movable between an open position readily receiving a hypodermic syringe plunger between the stop arms and a closed position permitting axial movement of the plunger but engaging and restraining the usual enlarged head or button on the syringe plunger to effect the retraction aspirating stroke.

Another object of the invention is the provision of a hypodermic syringe support and operating device as described in the preceding paragraphs, wherein the contact foot formation adapter to be placed against the skin of the patient or user is shaped to achieve a snap fit with an aligning collar on an insulin bottle or the like, achieving proper alignment of the components to simplify insertion of the needle into the insulin bottle for loading a measured dose of insulin or injection fluid into the syringe.

Other objects, advantages and capabilities of the present invention will become apparent from the following detailed description, taken in conjunction with the accompanying drawings illustrating a preferred embodiment of the invention.

BRIEF DESCRIPTION OF THE FIGURES

FIG. 1 is a perspective view of a syringe support and operating device embodying my invention, showing the syringe in broken lines and the device in the cocked position with the caliper-type stop arms closed;

FIG. 2 is a front elevational view thereof, with the device in cocked position;

FIG. 3 is a side elevational view thereof, with the syringe shown in broken lines in process of being inserted and the slide carriage for the syringe in uncocked or injection position;

FIG. 4 is a top plan view thereof viewed from the right of FIG. 2, with the caliper type stop legs shown in open position in broken lines;

FIG. 5 is a bottom end view thereof;

FIG. 6 is a vertical section view taken along the line 6—6 of FIG. 2;

FIG. 7 is a rear elevational view of the device;

FIG. 8 is a side elevational view thereof, viewed from the opposite side as FIG. 3; and FIG. 9 is a fragmentary exploded perspective view of the foot pad end portion of the device and an alignment collar and insulin bottle associated therewith.

DETAILED DESCRIPTION OF A PREFERRED EMBODIMENT

Referring to the drawings, wherein like reference characters designate corresponding parts throughout the several figures, the automatically aspirating hypodermic syringe supporting and operating device of the present invention is indicated generally by the reference character 10, and is designed for use with a conventional syringe 11 which may be of the usual configuration, having an axially elongated barrel portion 12 forming an elongated cylinder, with a hypodermic needle 13 projecting from the front end of the barrel or cylinder 12 and a reciprocative plunger 14 which extends into the barrel 12 and protrudes from the rear end thereof. The barrel or cylinder 12 in the illustrated embodiment is of uniform outer diameter throughout its length from the bottom or needle end thereof to the top or plunger end of the barrel or cylinder 12 and terminates at the latter end in an enlarged generally cylindrical collar 15a having diametrically oppositely extending flange formations 15b, usually having outwardly convergent sides and forming what are frequently referred to as finger pads. The barrel or cylinder portion 12 which is designed to be loaded with the insulin or dose of fluid to be injected is provided with the usual graduation markings and numeral indicia indicating the amount of insulin or other fluid to be loaded into the barrel and then injected into the patient.

The syringe supporting and operating device 10 of the illustrated embodiment is made of several components stamped from sheet metal of suitable rigidity and shaped by conventional shaping equipment, and includes a main plate member 16 in the form of a relatively thin elongated plate of generally rectangular shape having an outwardly projecting shallow flange 17 along one edge thereof, which is preferably knurled to facilitate holding of the main plate member and has a latch and trigger member 18 pivoted at the opposite edge thereof. The latch and trigger member 18 is provided with a concave flange formation 19 which is also knurled, in the illustrated embodiment, located in one direction from the pivot aperture 20 and having a rearwardly projecting catch tongue 21 at the opposite end portion extending through a slot 22 in the main plate member 16. The latch and trigger member 18 is pivotally supported and fastened on the main plate member 16 by a staple-like fastening strap 23 of sheet metal similar to that of the main plate member, having tabs at opposite ends thereof, one of which, indicated at 23a, extends through an appropriate portion of the slot 22 and is bent rearwardly of the plate member 16 toward the front or foot end of the mechanism, while the other bendable tab 23b extends through the pivot aperture 20 forming the pivot therefor, and through a slot therefor in the main plate member 16, and is bent rearwardly toward the opposite end of the mechanism. The tab 23b provides support for loop formations of a wire spring 24, having a pair of legs, one leg of which extends through and is restrained against an edge of the slot 22 and the other leg having an end portion bent around part of the catch tongue 21, to resiliently bias the latch and trigger member 18 in a counterclockwise direction as viewed in FIG. 2 toward the latching position.

A slide carriage assembly 25 is supported for rectilinear reciprocative movement on and longitudinally of the main plate member 16, and comprises a slidable syringe carrier member 26 including an elongated rigid base plate portion 27, an apertured front holder formation 28 extending outwardly from one end of the base portion 27 and a slotted rear holder formation 29 extending outwardly from the opposite end of the base portion 27. The front holder formation 28 is provided with a circular aperture 28a to receive needle the end portion of the barrel or cylinder 12 of the syringe therethrough. The slotted rear holder formation 29 is in the form of a slotted yoke-shaped structure having the outwardly opening slot 29a to receive the rear or plunger end portion of the barrel or cylinder 12 immediately below the finger pad forming flanges 15b thereof. The opposite lateral edge portions of the yoke-shaped rear holder formation are provided with bent flanges 30 which open inwardly toward the slot 29a to receive and hold the finger pad flange formations 15b of the syringe. The lateral or longitudinal edges of the elongated base plate portion 27 of the syringe carrier member 26 have downturned lateral flanges 31 forming shallow flange formations with edge portions bearing against the outwardly facing surface of the main plate member 16 and include pairs of bendable guide and securing tabs 32 which extend through pairs of elongated guide slots in the main plate member 16 and through small slots sized to receive the tabs 32 in oppositely projecting lateral flange portions 34 of a spring cover member 35 bearing against the back surface of the main plate member 16. The tabs 32 are bend rearwardly behind the flange formations 34 of the spring cover member 35 to secure the spring cover member 35 and syringe carrier member 26 in assembled relation. The central portion of the spring cover member 35 is provided with a U-shaped spring housing channel formation 36 to house a coil spring 37, one end of which is bent and caught over the upper edge of the spring housing channel formation 36 and the lower edge of which in the illustrated embodiment is provided with a hook-shaped end hooked through the upper end of a central slot 38 in the main plate member 16 for adjustably positioning a contact foot member to be later described.

Extending upwardly from the top or plunger end portion of the main plate member 16 is a longitudinally adjustable support bracket assembly 40 including a rigid support bracket member 41 having an elongated mounting leg 42, a short laterally extending leg formation 43, and an upwardly extending stop assembly mounting leg 44 joined to the laterally extending leg formation 43 and lying in a plane perpendicular to the planes of the legs 42, 43 and of plate 16. The elongated mounting leg 42 has a central slot 45 extending over most of its length flanked by shallow graduation indentation marks 45a and supported at longitudinally adjusted positions on the main plate member 16 by an adjustment screw 46 extending through an aperture for the threaded shank portion and into a clamping nut 46a. The upper end portion of the stop mechanism supporting leg 44 has a mounting platform flange formation 47 extending back toward the longitudinal center axis of the main plate member 16 and provided with pivot-forming apertures to receive pivot-forming bendable tabs 49 on opposite ends of a staple-like fastening strap 50, the tabs 49 also extending through pivot forming holes 51a, 52a in two pivoted caliper-like stop arms 51, 52.

The caliper-like stop arms have anchor holes 51b, 52b for receiving hooked end portions of a torsion spring wire 53 having two plural turn loop formations 53a, 53b therein through which the bendable tabs 49 extend, and arranged to resiliently urge the caliper-like stop arms 51, 52 away from each other to the open position shown in broken lines in FIG. 4. The outer free end portions of the caliper-like stop arms 51, 52 are provided with concave recesses 51c, 52c collectively forming a generally circular recess for receiving the stem of the plunger 14 of the syringe, and have stop shoulder formations 51d, 52d on the opposite ends thereof designed to bear against a shaped control cam formation 54 on a spring biased control slide member 55. The control slide member 55 is mounted against the rear or underside of the support leg portion 44 of the support bracket member 41 and has a pair of guide slots 55a therein through which extend guide and fastening tab formations 56 on opposite ends of a staple-like fastening strap 57 which extend through the slots 55a and anchoring holes in the support leg 44 and are bent into fastening position as shown. The control slide member 55 also has a right angle finger piece extension 58 terminating in a flat flange portion 58a which bears against one end of a coil spring 59 whose other end is fitted onto an anchoring stub formation 43a on the laterally extending leg portion 43. The upper end of the spring 59 adjacent the flange formation 58a may be retained in place by a shallow anchoring bulge or protrusion indented on the finger piece 58a.

Adjustably mounted on the lower or front end portion of the main plate member 16 is a contact foot formation 60, which is an angled elongated metal member of similar material to the main plate member 16 and bracket member 41, and comprises a mounting leg portion 61 having a tongue or depression which fits into slot 38 in the main plate member 16, also flanked by graduation indentation marks, and is fixed in position by an adjustment screw 63 extending through the mounting leg portion 61 and threaded into a clamping nut 64. Extending outwardly from leg portion 61 of the contact foot formation 60 is a shaped flange forming a foot pad, indicated by the reference character 65, which is provided with a slot 66 through which the needle 13 projects and a rounded periphery portion 67 defining an approximately three-quarter-round formation to achieve a snap interfit with a flexibly deformable plastic aligning collar 68 to be removably fitted onto the cap portion of the insulin bottle. The plastic aligning collar 68 is in the shape of an interrupted cylindrical band of slightly less than three-quarter round circumferential span having an inner diameter closely approximating the diameter of the rounded periphery portion 67 and having inwardly projecting lips or beads 67a, 67b at its opposite ends spaced axially apart a distance corresponding to the axial thickness of a usual insulin bottle cap plus the thickness of the foot pad flange 65. With such a collar 68 snapped onto the insulin bottle cap, the foot pad flange 65 can be readily snap-fitted into the collar 68 between the upper lip 67a and the bottle cap to facilitate alignment of the needle 13 in centered relation with the top of the bottle.

The injector device herein described in addition to automatically aspirating the syringe, has an additional feature in which the dose may be measured automatically, which will be of great assistance to persons with poor eyesight, and will help avoid mistakes in dosage. Assuming the injector device as shipped is set for a 50 unit dose, which is the customary practice, the autoaspirator and measured dose feature is adjusted by the user who requires a different number of units by the procedure now described. The set screw 46 associated with the clamping nut 46a for locating the bracket mounting leg 42 is loosened and the support bracket member 41 is extended to its limit position. The syringe plunger is set at the proper dose for the patient, and the needle end portion of the syringe barrel 12 is inserted into the opening 28a of the front holder formation 28 of the slide carriage 25. The finger pad flange formations 15b of the syringe are positioned approximately perpendicular to the plane of the injector device and aligned with the channel forming flanges 30 of the rear holder formation 29, and are pressed down firmly with the thumb into the channels formed by the rear holder 29. With the caliper-like stop arms 51, 52 in closed position, and being careful not to change the setting on the syringe, the stop arm supporting bracket member 41 is adjusted axially of the mounting leg 42 so that the underside of the caliper-like stop arms 51, 52 just touch the top of the enlarged button 14a on the syringe plunger 14. The set screw 46 is then tightened to fix the support bracket assembly 40 at this position of adjustment. The slide carriage 25 during this operation is at the injection or uncocked position.

To fill a needle with the appropriate dose determined by this setting of the device, the empty syringe with the plunger at the fully discharged position is inserted in the front and rear holders 28 and 29 in the manner previously described, and with the caliper-like stop arms 51, 52 in the closed position, the syringe plunger 14 is drawn back until the top of the plunger button touches the caliper-like stop arms 51, 52.

With the injector held, for example, in the left hand, with the palm of the hand to the front of the injector device, and using the right thumb on the inclined knurled pad surface 36a of the channel portion 36 of the spring cover member 35 and the right forefinger on the pad 58a controlling the stop arms 51, 52, squeezing pressure is applied to these pads, causing the pad 58a to depress first and open the caliper-like stop arms, and the thumb on the pad 36a and the finger on the pad 58a are continued to be squeezed together until the injector device is cocked by movement of the slide carriage assembly 25 to the FIG. 2 position where the catch tongue 21 of the latch and trigger member 18 is interfitted in the latch notch 34a in the adjacent flange portion 34 of the cover member 35.

The aligning collar 68 is then snapped onto the top of the insulin bottle, the top of the insulin bottle is sterilized, and holding the bottle in the left hand and the injector in the right, the part-round portion of the foot pad flange 65 is snapped into fully inserted position in the aligning collar 68, and the trigger 18 is pressed which will release the spring driven slide carriage assembly 25 and the syringe barrel and needle carried thereby, driving the needle into the bottle. Holding the injector so that the bottle is in an up position the syringe plunger is then pushed to bottom or fully discharge position which forces measured air into the bottle. The caliper-like stop arms 51, 52 are then closed by finger pressure on their outside edges, the injector and attached bottle are positioned so the bottle is upside down, and the plunger is positioned to force any air out of the syringe. The syringe plunger is then pulled back slowly until it just touches the caliper-like stop arms, thus drawing into the syringe barrel from the bottle the appropriate dosage of insulin. Fingers squeezing against the pad 36a and the pad 58a then causes the caliper-like stop arms 51, 52 to release to the open position and continued squeezing moves the slide carriage assembly 25 to the cocked position. This movement also withdraws the needle from the insulin bottle and the bottle is then rotated with the aligning collar to remove the bottle from the foot pad flange 65.

After using alcohol or the like on the spot to be injected, the injector device is positioned to place the foot pad flange 65 against the skin of the patient and the trigger 18 is squeezed to release the slide carriage assembly 25 to be spring driven to the injection position injecting the needle into the patient. In the illustrated embodiment, the surface of the foot pad flange 65 facing the skin of the user is knurled to retard slipping. Aspiration automatically occurs during the injection stroke of the slide carriage assembly 25, because the underside of the plunger button or enlarged head is engaged by the upper surfaces of the stop arms 51, 52, effecting a short retraction of the plunger from the measured dose position over an axial distance equal to the thickness of the plunger button 14a plus the thickness of the stop arms 51, 52. If the needle has entered a vein during the injection stroke, some blood will be drawn into the syringe giving immediate visible evidence of this positioning of the needle. Since one must never inject insulin directly into a vein, the patient or operator then moves the injector mechanism to withdraw the needle, and the syringe is removed and destroyed, and a new loading and injection operation is repeated until no blood shows. When the needle has been properly injected and no blood shows, the caliper-like stop arms of the injector device are then opened by pressing the pad 58a with the right forefinger, and the plunger top button is then moved to discharge the insulin or hypodermic fluid into the area being injected, by finger squeezing pressure on the knurled rear syringe holder formation 29 and the plunger button. After slowly forcing the insulin into the area being injected, the needle is withdrawn, and the syringe is withdrawn from the holder formations 28, 29 and destroyed.

I claim:

1. An auto-aspirating hypodermic syringe supporting and operating device for self-administered injection of hypodermic medication, insulin or the like, the hypodermic syringe including a barrel, a plunger projecting from a rear end thereof having a smaller diameter shaft portion and an enlarged head, and a needle projecting from a front end of the barrel; the device comprising an elongated thin main plate member having longitudinal slots, a carriage assembly slidably mounted on said plate member for reciprocative longitudinal movement through projecting and retracting strokes, said carriage assembly including a spring biased syringe carrier member slidably carried against one face of the plate member and having front and rear holder portions projecting therefrom to removably receive and hold end portions of the barrel and a back member fixed to said syringe carrier member by fastener tabs extending through said slots to slide longitudinally with said carrier member, a pivoted latch trigger member pivoted on said plate member having a finger operated trigger portion and a latch formation to latch the carriage assembly in a cocked position, a stop supporting bracket extending from said plate member alongside the plunger path having movable stop members extending therefrom in a plane perpendicular to the plunger path, and stop positioning means on said bracket for disposing said stop members at a head-intercepting first position near the plunger shaft between the head formation and said barrel when the plunger is retracted to predetermined dosage position and locating the stop members at an open second position admitting passage of said head therebetween, the stop members being spaced from carrier member when adjusted for the proper dosage to engage said head and cause relative short retracting movement of the plunger during the terminal portion of said projecting stroke to cause withdrawal of blood into the syringe barrel if the tip of the needle is lodged in a vein.

2. An auto-aspirating hypodermic syringe supporting and operating device as defined in claim 1, wherein said syringe barrel has a pair of oppositely projecting finger pad forming flanges, said front holder portion of said carrier member being a thin plate flange formation having a hole therethrough sized to correspond substantially to and receive said barrel, and said rear holder portion comprising a slotted yoke-shaped formation providing a pair of bent flanges defining a pair of spaced inwardly facing channels to slidably receive the finger pad forming flanges of said barrel.

3. An auto-aspirating hypodermic syringe supporting and operating device as defined in claim 1, wherein said syringe barrel has a pair of oppositely projecting finger pad forming flanges, said front holder portion of said carrier member being a thin plate flange formation having a hole therethrough sized to correspond substantially to and receive said barrel, and said rear holder portion comprising a slotted yoke-shaped formation providing a pair of bent flanges defining a pair of spaced inwardly facing channels to slidably receive the finger pad forming flanges of said barrel, and a contact foot member extending from said plate member formed of an angled elongated sheet metal strip providing a first leg fastened to the plate member in coplanar relation thereto and a flange-like second leg projecting in near-right-angular relation therefrom forming a foot pad to engage the skin of the user and having an aperture for passage of the needle therethrough.

4. An auto-aspirating hypodermic syringe supporting and operating device as defined in claim 1, wherein said back member forms a spring housing member having an elongated channel portion shaped to house a coil spring and a pair of oppositely projecting flat flange portions flanking the channel portion located in coplanar relation to said plate member against a back face of the plate member and fixed to said carrier member by said tab, said channel portion having an elongated coil spring therein connected to one end thereof and to said plate member.

5. An auto-aspirating hypodermic syringe supporting and operating device as defined in claim 2, wherein said back member forms a spring housing member having an elongated channel portion shaped to house a coil spring and a pair of oppositely projecting flat flange portions flanking the channel portion located in coplanar relation to said plate member against a back face of the plate member and fixed to said carrier member by said tab, said channel portion having an elongated coil spring therein connected to one end thereof and to said plate member.

6. An auto-aspirating hypodermic syringe supporting and operating device as defined in claim 3, wherein said back member forms a spring housing member having an elongated channel portion shaped to house a coil spring and a pair of oppositely projecting flat flange portions flanking the channel portion located in coplanar relation to said plate member against a back face of the plate member and fixed to said carrier member by said tab, said channel portion having an elongated coil spring therein connected to one end thereof and to said plate member.

7. An auto-aspirating hypodermic syringe supporting and operating device as defined in claim 3, wherein said second leg has a rounded periphery portion defining a substantially three-quarter-round edge to be interfitted in a flexibly deformable plastic aligning collar shaped to be removably fitted onto a cap portion of an insulin bottle from which the dosage is to be withdrawn.

8. An auto-aspirating hypodermic syringe supporting and operating device as defined in claim 6, wherein said second leg has a rounded periphery portion defining a substantially three-quarter-round edge to be interfitted in a flexibly deformable plastic aligning collar shaped to be removably fitted onto a cap portion of an insulin bottle from which the dosage is to be withdrawn.

9. An auto-aspirating hypodermic syringe supporting and operating device as defined in claim 1, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

10. An auto-aspirating hypodermic syringe supporting and operating device as defined in claim 2, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

11. An auto-aspirating hypodermic syringe supporting and operating device as defined in claim 3, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

12. An auto-aspirating hypodermic syringe supporting and operating device as defined in claim 4, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

13. An auto-aspirating hypodermic syringe supporting and operating device as defined in claim 5, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

14. An auto-aspirating hypodermic syringe supporting and operating device as defined in claim 6, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

15. An auto-aspirating hypodermic syringe supporting and operating device as defined in claim 7, wherein said stop members on said stop supporting bracket are formed by a pair of caliper-like stop arms pivotally mounted on said bracket and extending therefrom in a plane perpendicular to the path of movement of the syringe plunger for swinging movement toward and away from each other in said plane, said device including spring means urging said stop arms to an open position freely accommodating passage of the syringe plunger head therebetween, and a control plate slidably mounted on said bracket having a shaped cam portion engaging portions of said stop arms to position them in a closed position adjacent and embracing the plunger shaft portion immediately below the head thereon and accommodating passage of the plunger shaft portion therebetween.

16. An auto-aspirating hypodermic syringe supporting and operating device as defined in claim 9, wherein said control plate has a finger actuated trip formation thereon and spring means extending between said trip formation and the bracket resiliently urging the control plate to a position maintaining said stop arms in said closed position, the stop arms being located relative to the rear holder formation of said carrier member to engage the head of the plunger during the projecting stroke of the carriage assembly.

17. An auto-aspirating hypodermic syringe supporting and operating device as defined in claim 11, wherein said control plate has a finger actuated trip formation thereon and spring means extending between said trip formation and the bracket resiliently urging the control plate to a position maintaining said stop arms in said closed position, the stop arms being located relative to the rear holder formation of said carrier member to engage the head of the plunger during the projecting stroke of the carriage assembly.

18. An auto-aspirating hypodermic syringe supporting and operating device as defined in claim 14, wherein said control plate has a finger actuated trip formation thereon and spring means extending between said trip formation and the bracket resiliently urging the control plate to a position maintaining said stop arms in said closed position, the stop arms being located relative to the rear holder formation of said carrier member to engage the head of the plunger during the projecting stroke of the carriage assembly.

19. In an auto-aspirating hypodermic syringe supporting and operating device as defined in claim 16, said stop supporting bracket including an elongated slotted slat-like mounting leg slidably disposed against a face of said plate member for longitudinal adjustment relative thereto, and a screw passing through a slot of said mounting leg and a clamping nut fastener therefor for releasably fixing said mounting leg to said plate member over a predetermined range of adjustment positions.

20. In an auto-aspirating hypodermic syringe supporting and operating device as defined in claim 16, said stop supporting bracket including an elongated slotted slat-like mounting leg slidably disposed against a face of said plate member for longitudinal adjustment relative thereto, and a screw passing through a slot of said mounting leg and a clamping nut fastener therefor for releasably fixing said mounting leg to said plate member over a predetermined range of adjustment positions.

* * * * *